US006305380B1

United States Patent
Hellstrand et al.

(10) Patent No.: US 6,305,380 B1
(45) Date of Patent: *Oct. 23, 2001

(54) METHOD FOR TREATMENT OF CANCER AND INFECTIOUS DISEASE

(75) Inventors: Kristoffer Hellstrand, Göteborg; Svante Hermodsson, Mölndal, both of (SE)

(73) Assignee: Maxim Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/574,874

(22) Filed: May 19, 2000

Related U.S. Application Data

(63) Continuation of application No. 09/465,432, filed on Dec. 21, 1999, now Pat. No. 6,155,266, which is a continuation of application No. 09/033,110, filed on Mar. 2, 1998, now Pat. No. 6,003,516, which is a continuation of application No. 08/374,787, filed on May 8, 1995, now Pat. No. 5,728,378.

(51) Int. Cl.[7] .................................................. A61B 19/00
(52) U.S. Cl. ............................................................ 128/898
(58) Field of Search .......................... 128/898; 424/85.7, 424/85.4; 530/351

(56) References Cited

U.S. PATENT DOCUMENTS

| 4,863,727 | 9/1989 | Zimmerman et al. . |
| 4,883,661 | 11/1989 | Daly et al. . |
| 4,997,645 | 3/1991 | Suzuki et al. . |
| 5,026,544 | 6/1991 | Albrecht et al. . |
| 5,215,744 | 6/1993 | Suzuki et al. . |

FOREIGN PATENT DOCUMENTS

| 7165582 | 6/1995 | (JP) . |

OTHER PUBLICATIONS

Burtin et al., "The influence of intraperitoneal injections of Histamine on Tumour Growth in Fibrosarcoma–Bearing Mice", *Cancer Letters*, 12: 195–201, Jan. 1981.

Osband et al., "Successful Tumour Immumotherapy with Cimetidine in Mice", *The Lancet*, No. 8221, 1: 636–638, Mar. 21, 1981.

Seaman et al., "Suppression of Natural Killing in Vitro by Monocytes and Polymorphonuclear Leukoctues", *The Journal of Clinical Investigation*, 69: 876–888, Apr. 1982.

Dempsey et al., "The Differential Effects of Human Leukocytic Pyrogen/Lymphocyte–Activating Factor, T Cell Growth Factor, and interferon on Human on Human Natural Killer Activity", *The Journal of Immunology*, May 17, 1982.

Barna et al. "Tumor–Enhancing of Cimetidine". *Oncology*, 40: 43–45, 1983.

Thornes et al., "Combination of Cimetidine with other Drugs for Treatment of Cancer", *New England Journal of Medicine*, 308: 591–592, Mar. 10, 1983.

Beer et al., "The Influence of Histamine on Immune and Inflammatory Responses", *Advances in Immunology*, 35: 209–268, 1984.

Lespinatas et al., "Enhancement by serotonin of intra–tumour penetration of spleen cells", *Br. J. Cancer*, 50: 545–547, Apr. 5, 1984.

Dohlsten et al., "Histamine Inhibits Interferon–γProduction via Suppression of Interleukin 2 Synthesis", *Cellular Immunology*, 101: 493–501, 1986.

(List continued on next page.)

Primary Examiner—Dinh X. Nguyen
(74) Attorney, Agent, or Firm—Knobbe, Martens, Olson & Bear

(57) ABSTRACT

In a method of treating a viral infection involving activation of NK cells, the improvement comprising administering to a patient receiving such treatment an effective NK-cell-activity facilitating amount of a histamine $H_2$ or $5\text{-}HT_{1A}$ receptor agonist.

18 Claims, 2 Drawing Sheets

OTHER PUBLICATIONS

Nair et al., "Histamine–Induced Suppressor Factor Inhibition of NK Cells: Reversal with Interferon and Interleukin 2", *The Journal of Immunology*, 136(7): 2456–2462, Apr. 1, 1986.

Hellstrand et al., "Histamine $H_2$–Receptor–Mediated Regulation of Human Natural Killer Cell Activity", *The Journal of Immunology*, 137(2), Jul. 15, 1986.

Hellstrand, "Biogenic Amine in the Regulation of Human Natural Killer Cell Cytotoxicity" Published by Medi Press Research Reports, Printed by Novem Grafiska AB, Göteborg 1987.

Hellstrand et al., "Differential Effects of Histamine Receptor Antagonists on Human Natural Killer Activity", *Int. Archs Allergy Appl. Immunology* 84: 247–255, 1987.

Richtsmeier et al., "Selective, Histamine–Mediated Immunosuppression in Laryngeal Cancer", *Ann. Otol. Rhinol. Laryngol.*, 96(5): 569–572, 1987.

Burtin et al., "Clinical Improvement in Advanced Cancer Disease After Treatment Combining Histamine and $H_2$–Antihistamatics (Ranitidine or Cimetidine)" Accepted Jun. 1987.

Hellstrand et al., "Role of Serotonin in the Regulation of Human Natural Killer Cell Cytotoxicity", *The Journal of Immunology*, 139(3), Aug. 1, 1987.

Urba et al., "Enhancement of Natural Killer Activity in Human Peripheral Blood by Flavone Acetic Acid", *The Journal of the National Cancer Institute*, 80(7): 521–525, Jun. 1, 1988.

Hornung et al., "Augmentation of Natural Killer Activity, Induction of IFN and Development Tumor Immunity During the Successful Treatment of Established Murine Renal Cancer Using Flavone Acetic Acid and IL–2", *The Journal of Immunology*, 141(10): 3671–3679, Nov. 15, 1988.

Ostensen et al., "Enhancement of Human Natural Killer Cell Function by the Combined Effects of Tumor Necrosis Factor α or Interleukin–1 and Interferon–α or Interleukin–2", *Journal of Biological Response Modifiers*, 8: 53–61, 1989.

Hellstrand et al., "Suppression of human natural killer cell cytotoxicity by interleukin–2", *Clin. Exp. Immunol.*, 77: 410–416, 1989.

Alam et al., "Comparative Effect of Recombinant IL–1, –2, –3, –4, and –6, IFN–γ, Granulocyte–Macrophage–Colony–Stimulating Factor, Tumor Necrosis Factor–α, and Histamine–Releasing Factors on the Secretion of Histamine from Basophils", *The Journal of Immunology*, 142(10): 3431–3435, May 18, 1989.

Schleimer et al., "Regulation of Human Basophil Mediator Release by Cytokines", *The Journal of Immunology*, 143(4): 1310–1317, Aug. 15, 1989.

Hellstrand et al., "A Cell–to–Cell Mediated Interaction Involving Monocytes and Non T/CD16+ Natural Killer (NK) Cells is Required for Histamine $H_2$–Receptor–Mediated NK–Cell Activation", *Scand. J. Immunol.*, 31: 631–644, 1990.

Hellstrand et al., "Enhancement of Human Natural Killer Cell Cytotoxicity by Serotonin: Role of Non–T/CD176+ NK Cells, Accessory Monocytes, and 5–HT 1A Receptors", *Cellular Immunology*, 127: 199–214, 1990.

Hellstrand et al., "Monocyte–Mediated Suppression of IL–2–Induced NK–Cell Activation", *Scand. J. Immunol.* 32: 183–192, 1990. *Int. Arch. Allergy Appl. Immunotherapy*, 92: 379–389, 1990.

Hellstrand et al., "Synergistic Activation of Human Natural Killer Cell Cytotoxicity by Histamine and Interleukin–2".

Tom Smith, MD, "Histamine Type 2–Receptor Antagonists and Cancer Immunotherapy", *Comprehensive Therapy*, 16(1): 8–13, 1990.

Krigel et al., "Renal Cell Carcinoma: Treatment with Recombinant Interleukin–2 Plus Beta–Interferon", *Journal of Clinical Oncology*, 8(3): 460–467, Mar. 1990.

Hellstrand et al., Role of Histamine in Natural Killer Cell––Mediated Resistance Against Tumor Cells:, *The Journal of Immunology*, 145(12), Dec. 15, 1990.

Hellstrand et al., "Cell–to–Cell Mediated Inhibition of Natural Killer Cell Proliferation by Monocytes and its Regulation by Histamine $H_2$–Receptors", *Scand. J. Immunol.*, 34: 741–752, 1991.

Hellstrand et al., "Monocyte–Induced Down–Modulation of CD16 and CD56 Antigens on Human Natural Killer Cells and its Regulation by Histamine $H_2$–Receptors", *Cellular Immunology*, 138: 44–45, 1991.

Schantz et al., "A phase II study of interleukin–2 and interferon–alpha in head and neck cancer", *Investigation New Drugs*, 10: 217–223, 1992.

Hellstrand et al., "Regulation of Natural Killer Cell Response to Interferon–α by Biogenic Amines", *Journal of Interferon Research*, 12:199–205, 1992.

Budd et al., "Phase I Trial of High–Dose Bolus Interleukon–2 and Interferon Alfa–2 in Patients with Metastatic Malignancy", *Journal of Clinical Oncology* 10(5): 804–809, May 1992.

Ilson et al., "A Phase II Trial of Interleukin–2 and Interferon Alfa–2a in Patients with Advanced Renal Cell Carcinoma" *Journal of Clinical Oncology*, 10(7): 1124–1130, Jul. 1992.

Saarloos et al., "Effects of histamine type–2 receptor antagonists on indomethacin and IL–2 immunotherapy of metastasis" *Clin. Exp. Metastasis*, 11: 275–283, 1993.

Hellstrand et al., "Serotonergic 5–HT $_{1A}$ Receptors Regulate a Cell Contact–Mediated Interaction between Natural Killer Cells and Monocytes", *Scand. J. Immunol.*, 37: 7–18, 1993.

Hellstrand et al., "Histamine in Immunotherapy of advanced melanoma: a pilot study", *Cancer Immunol. Immunother*, 39: 416–419, 1994.

Chun, Myung et al., "Modulation of Interferon–Induced NK Cells by Interleukin 2 and cAMP", *Lymphokine Research*, 1(4): 91–98, 1982. Abstract only.

METHOD FOR TREATMENT OF CANCER AND INFECTIOUS DISEASE

CROSS REFERENCE TO RELATED APPLICATIONS

This application is a continuation of U.S. patent application Ser. No. 09/465,432, filed on Dec. 21, 1999, now U.S. Pat. No. 6,155,266 which is a continuation of U.S. patent application Ser. No. 09/033,110, filed Mar. 2, 1998, now U.S. Pat. No. 6,003,516 which is a continuation of U.S. patent application Ser. No. 08/374,787, filed May 8, 1995, now U.S. Pat. No. 5,728,378.

FIELD OF THE INVENTION

The present invention concerns a pharmaceutical preparation or system for activation of natural killer cells (NK-cells), in order, for example, to treat tumors or virus infections.

BACKGROUND OF THE INVENTION

Natural killer cells (NK-cells) are a group of spontaneously cytotoxic lymphocytes that destroy tumor cells by lysis with no antigen specificity or restriction by histocompatibility molecules. Monocytes are involved in the regulation of the NK-cell's function, both through mechanisms involving cell contact and through providing soluble NK cell-regulating mediators. Recently, a cell contact-mediated mechanism has been described whereby monocytes regulate NK-cells. This type of monocyte-mediated regulation is exerted by monocytes that are obtained directly from peripheral blood through counterflow centrifugal elutriation (CCE) and is regulated by the biogenic amines histamine and serotonin (Hellstrand and Hermodsson, 1986, J. Immunol. 137, 656–660; Hellstrand and Hermodsson, 1987, J. Immunol. 139, 869–875; Hellstrand and Hermodsson, 1990, Scand. J. Immunol. 31, 631–645; Hellstrand and Hermodsson, 1990, Cell. Imnmunol. 127, 199–214; Hellstrand, Kjellson and Hermodsson, 1991, Cell. Imrnunol., 138, 44–54). These NK-cell regulating mechanisms caused by biogenic amines should be of importance to the NK-cell-mediated defense against metastatic tumors in vivo (Hellstrand, Asea and Hermodsson (1990), J. Immunology 145, 4365–4370).

Interferon-α(IFN-α) is an important regulating factor for NK cells. It effectively enhances the NK cell's cytotoxicity (NKCC) both in vivo and in vitro (Trinchieri, 1989, Adv. Immunol. 47,187–376; Einhorn, Blomgren and Strander, 1978, Int. J. Cancer 22, 405–412; Friedman and Vogel, 1984, Adv. Immunol., 34, 97–140).

Owing to the high rate of cancer and the only partially successful treatment methods available today, there is a constant demand for other improved methods of treatment of tumors. There is also a great demand for improved treatment methods for virus infections.

SUMMARY OF THE INVENTION

The goal of the invention is to create a pharmaceutical preparation or system that effectively stimulates NK cells, e.g., in order to treat tumors, primarily myelomas, renal cancer, leukemias and melanoma, or to treat virus infections, primarily chronic hepatitis B and hepatitis C. The preparation or system according to the invention involves a first composition, containing interferon-α or analogues thereof, and a second composition containing at least one substance with histamine $H_2$, or serotonin 5-$HT_{1A}$ receptor agonist activity, whereby said first and second compositions are either mixed in a preparation or supplied in separate doses in an amount sufficient for the intended treatment. The invention also comprises a method for treatment of viral or neoplastic disease comprising the step of coadministering interferon-α and an effective amount of a histamine $H_2$ receptor agonist or a serotonin 5-$HT_{1A}$ receptor agonist. Furthermore, the invention includes a method for the treatment of viral infection comprising administering a histamine $H_2$ receptor agonist or a 5-$HT_{1A}$ receptor agonist.

The invention shall be described in greater detail below, making reference to reported in vitro experiments.

DETAILED DESCRIPTION OF THE PREFERRED EMBODIMENTS

Figure 1:
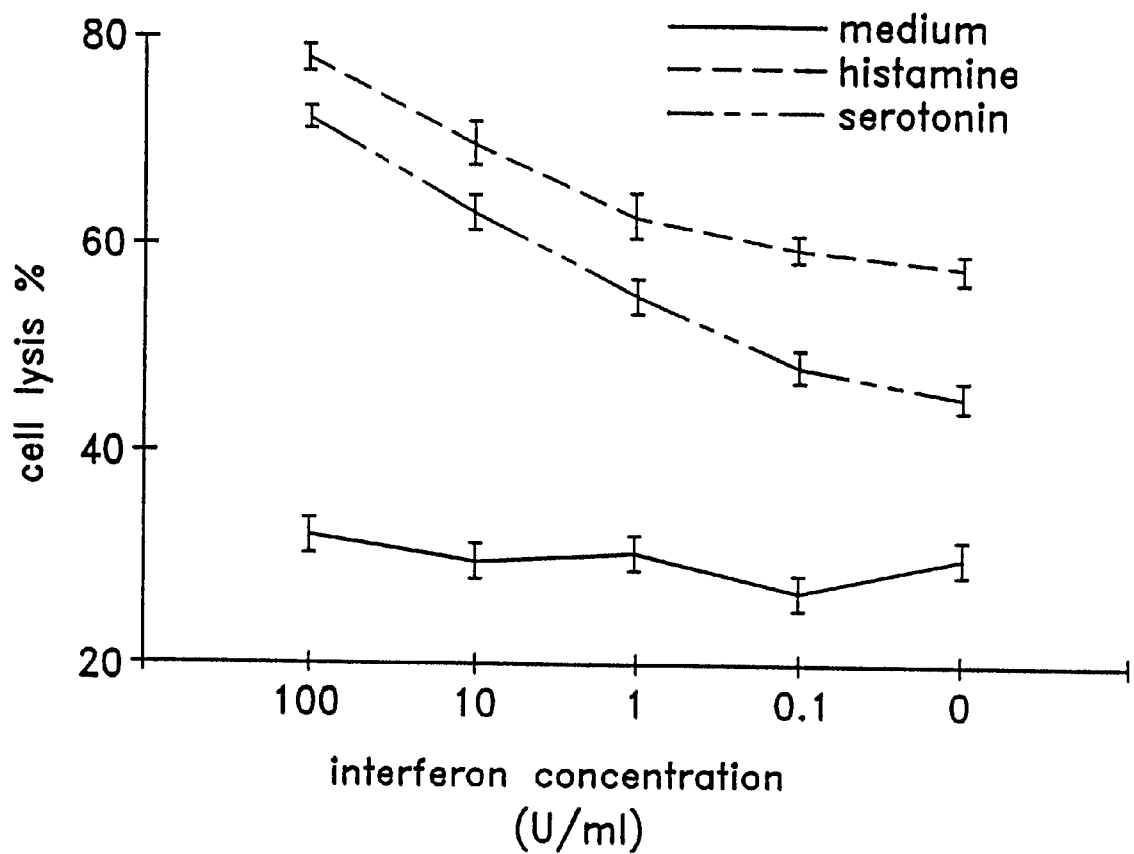
FIG. 1 shows in graph form the synergistic NK cell activation against cultured target cells produced by IFN-α and histamine or serotonin for various concentrations of IFN-α(0–100 U/ml).

The invention is based on the unexpected discovery that IFN-α and the biogenic amines histamine and/or serotonin produce a synergistic activation of NK cells.

The experiments reported hereafter show that eluted monocytes effectively suppress the activation of NK cells induced by IFN-α. Furthermore, it is shown that histamine or serotonin, which act through defined bioaminergic receptors, remove the monocyte induced suppression and thereby restore the ability of the NK cells to respond to IFN-α.

Analogues of histamine with H2-receptor agonist activity or other compounds with H2-receptor agonist activity and analogues of serotonin with 5-$HT_{1A}$-receptor agonist activity or other compounds with 5-$HT_{1A}$-receptor agonist activity that are suitable for use in the present invention are known within the art and shall not be described more closely here. For example, these analogues can have a chemical structure resembling that of histamine or serotonin, but modified by addition of groups that do not negatively affect the $H_2$ or 5-$HT_{1A}$ receptor activities. Known $H_2$-receptor agonists include histamine, dimaprit, clonidine, tolazoline, impromadine, 4-methylhistamine, betazole and histamine congener derivatives such as:

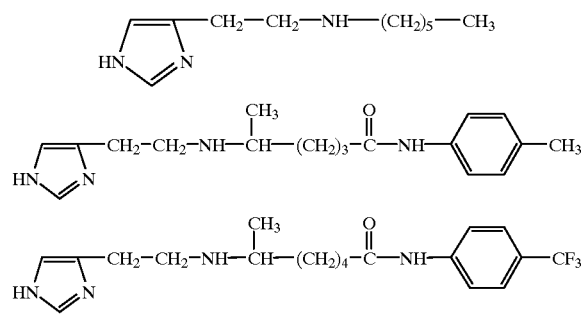

described as compounds 1, 6, and 9 in Khan et al., J. Immunol., Vol. 137 pp. 308–315. Known serotonin 5-$HT_{1A}$ receptor agonists include 8-OH-DPAT (8-hydroxy-2-(di-n- propylamino)tetralin), ALK-3 (cis-8-hydroxy-1-methyl-2-(di-n-propylamino)tetralin), BMY 7378 (8[2-[4-(2-methoxyphenyl)-1-piperazinyl]ethyl]-8-azaspiro[4,5]decane-7,9-dione), NAN 190 (1-(2-methoxyphenyl-4-[4-(2-phthalimmido)butyl]pierazine HBr), lisuride, d-LSD, flesoxinan, DHE (dihydroergotamine), MDL 72832 (8-[4-91,4-benzodioxan-2-ylmethyl-amino)butyl]-8-azaspiro[4,5]decane-7,9-dione), 5-CT (5-carboxamidotryptamine), DP-5-CT (N,N-dipropyl-5-carboxamidotryptamine), ipsapirone, WB 4101 (2-[[[2-(2,6-dimethoxyphenoxy)ethyl]amino]methyl]-1,4-benzodioxane), ergotamine, buspirone, metergoline, spiroxatrine, PAPP (1-[2-(4-aminophenyl)ethyl]-4-(3-trifluoromethylphenyl) piperazine), SDZ (–) 21009 ((4(3-terbutylamino-2-hydroxypropoxy)indol-2-carbonic-acid-isopropylester), and butotenine.

IFN-α and histamine/serotonin can be administered separately or in the same preparation. The method of administration can be either local or systemic injection or infusion. Other methods of administration can also be suitable.

The compounds can even be administered intraperitoneally or in another parenteral method. Solutions of the active compounds in the form of free acids or pharmaceutically acceptable salts can be administered in water with or without a tenside such as hydroxypropylcellulose. Dispersions making use of glycerol, liquid polyethyleneglycols, or mixtures thereof with oils can be used. Antimicrobial compounds can also be added to the preparation.

Injectable preparations may include sterile water-based solutions or dispersions and powders that can be dissolved or suspended in a sterile medium prior to use. Carriers such as solvents or dispersants containing, e.g., water, ethanolpolyols, vegetable oils and the like can also be added. Coatings such as lecithin and tensides can be used to maintain suitable fluidity of the preparation. Isotonic substances such as sugar or sodium chloride can also be added, as well as products intended to retard absorption of the active ingredients, such as aluminum monostearate and gelatin. Sterile injectable solutions are prepared in the familiar way and filtered before storage and/or administration. Sterile powders can be vacuum-dried or freeze-dried from a solution or suspension.

All substances added to the preparation must be pharmaceutically acceptable and essentially nontoxic in the quantities used. The preparation and formulations that produce a delayed release are also part of the invention.

The preparation is supplied in dosage units for a uniform dosage and to facilitate administration. Each dosage unit contains a predetermined quantity of active components to produce the desired therapeutic effect, along with the requisite quantity of pharmaceutical carriers.

IFN-α can be administered in a quantity of around 1000 to 300,000 U/kg/day, preferably around 3000 to 100,000 U/kg/day and more preferably, around 10,000 to 50,000 U/kg/day.

The compounds with $H_2$, and $5-HT_{1A}$ receptor agonist activity can be administered in a of quantity of around 0.1 to 10 mg/day, preferably around 0.5 to 8 mg/day and more preferably, around 1 to 5 mg/day. However other quantities can be administered with IFN-α as decided by the treating physician. For substances other than biogenic amines with corresponding receptor activity, doses producing an equivalent pharmacological effect shall be used.

Although it is stated in the examples that the administration was given in a single dose, it is obvious that the compounds can be distributed over longer periods of time for treatment of virus infections or tumors.

The daily dose can be administered as a single dose or it can be divided into several doses, should negative effects occur.

EXAMPLES

In Vitro Studies of IFN-α and histamine/serotonin.

This example illustrates the effect of human recombinant IFN-α and histamine/serotonin, separately and in combination, on the NK cell cytotoxicity (NKCC) for human mononuclear cells (MNC).

MNC were obtained from peripheral venous blood from healthy human blood donors by Ficoll-Hypaque centrifuging, followed by Percoll density-gradient fractionation (Timonen and Saksela, 1980, J. Immunol. Methods 36, 285–291; Hellstrand and Hermodsson, 1990, Scand. J. Immunol. 31, 631–645).

In the respective Percoll fractions, the high-density MNC (Percoll fractions 1–4) were small lymphocytes with low baseline cytotoxicity against K562 target cells. After removal of the monocytes, the low-density fractions 6–10 displayed high NKCC, consistent with earlier studies. (Timonen and Saksela, 1980, J. Immunol. Methods 36, 285–291).

The target cells used in these experiments were K562, an NK-cell sensitive erythroleukemic cell line, or Daudi, a relatively NK-insensitive EBV-transformed B-cell lymphoblastoid cell line.

The NKCC was determined six times as the specific $^{51}$Cr-release for a MNC: target-cell ratio of between 30:1 and 3.8:1 in two-fold dilution gradients. The suspensions of MNC/target cells were incubated in microplates at 37° C. for 6 hours (Daudi) or 16 hours (K562). The supernatant solution was then collected and examined for radioactivity in a gamma counter. The maximum $^{51}$Cr-release was measured in target cell cultures treated with Triton X-100. The NKCC was calculated as the cell lysis % by the formula 100× (experimental release–spontaneous release/maximum release–spontaneous release)=cell lysis %.

A low-density Percoll fraction was separated by counterflow centrifuge elusion (CCE) in a monocyte and in a lymphocyte fraction. The monocyte fraction was concentrated to >90% purity whereupon the contaminating cells consisted of large lymphocytes. The lymphocyte fractions obtained by CCE contained <3% monocytes, determined by morphology and Leu-M3 (CD14) antigen expression. The lymphocytes were CD3$^-$/16$^+$/56$^+$ T cells (45–50%), CD3$^-$/16$^-$/56$^-$ NK cells (35–40%), CD3$^+$/16$^-$/56$^-$ T cells (45–50%), CD3$^+$/16$^+$/56$^+$ cells (1–5%), determined by flow cytometry.

The eluted monocytes and/or the NK cell-concentrated low-density lymphocytes were treated with IFN-α and histamine/serotonin. The compounds were added, separately or in combination, to mixtures of MNC and K562 target cells at the start of a 16-hour $^{51}$Cr-release assay. The cytotoxicity against K562 in the NK cell-concentrated lymphocyte fraction was increased by IFN-α and unaffected by histamine or serotonin. The eluted monocyte fraction exhibited a low baseline cytotoxicity and was slightly induced by histamine/IFN-α or serotonin/IFN-α; this cytotoxicity resulted from the low fraction of contaminating lymphocytes (data not given). The addition of eluted monocytes to the NK cell concentrated lymphocytes suppressed the baseline cytotoxicity to K562. Furthermore, the eluted monocytes almost totally inhibited the activation of the cytotoxicity by means of IFN-α (Table 1).

Histamine and serotonin restored the basal cytotoxicity of lymphocytes in mixtures of monocytes and lymphocytes. Furthermore, both histamine and serotonin eliminated the monocyte induced inhibition of the NK cell response to IFN-α. Hence, IFN-α plus histamine or serotonin synergistically enhance the cytotoxicity in mixtures of monocytes and NK cell-enriched lymphocytes (Table 1).

In the experiments reported in Table 1, eluted lymphocytes were mixed with monocytes as shown in the table, in a total volume of 150 μl. The data are NKCC (mean±SEM) of six determinations. Serotonin $10^{-4}$ M and/or IFN-α (25 U/ml) was added at the start of a 16-hour microcytotoxicity test against $10^4$ K562 target cells.

IFN-α (0–100 U/ml). The data shown are NKCC (cell lysis %; mean ±SEM of six determinations). The compounds were added at the start of a 16 h microcytotoxicity test against K 562 target cells.

TABLE 2

Synergistic Activation of NK Cells by Histamine and IFN-α

| | | | | NKCC (cell lysis % ± SEM) Histamine concentration | | | |
|---|---|---|---|---|---|---|---|
| Exp | Target cell | MNC/target cell ratio | Treatment | 0 | $10^{-4}$ M | $10^{-5}$ M | $10^{-6}$ M |
| 1 | K 562 | 15:1 | Medium | 33.1 ± 0.5 | 55.5 + 1 | 54.7 ± 1 | 39.2 ± 1 |
|   |       |      | IFN 25 U/ml | 33.1 ± 1 | 76.4 ± 3 | 74.1 ± 1 | 66.0 ± 2 |
| 2 | K 562 | 15:1 | Medium | 20.7 ± 0.4 | 32.4 ± 1 | 27.4 ± 1 | 23.2 ± 2 |
|   |       |      | IFN 25 U/ml | 27.4 ± 1 | 67.9 ± 2 | 66.2 ± 1 | 55.4 ± 1 |
| 3 | K 562 | 15:1 | Medium | 31.4 ± 1 | 43.3 ± 1 | 38.6 ± 1 | 29.4 ± 1 |
|   |       |      | IFN 25 U/ml | 32.5 ± 1 | 71.9 ± 1 | 66.5 ± 2 | 56.3 ± 2 |
| 4 | Daudi | 30:1 | Medium | 1.0 ± 0.4 | 4.4 ± 1 | 3.5 ± 2 | 1.1 ± 0.3 |
|   |       |      | IFN 25 U/ml | 1.1 ± 0.5 | 31.7 ± 1 | 28.3 ± 1 | 14.1 ± 1 |
| 5 | Daudi | 30:1 | Medium | 2.2 ± 1 | 13.5 ± 1 | 9.7 ± 1 | 2.5 ± 1 |
|   |       |      | IFN 25 U/ml | 2.7 ± 1 | 61.3 ± 3 | 52.3 ± 2 | 31.7 ± 1 |

TABLE 1

Suppression of NK Cell Cytotoxicity by Monocytes and Elimination of This Effect with Serotonin

| Monocytes (× $10^{-4}$) | Lymphocytes (× $10^{-4}$) | NK CELL CYTOTOXICITY AFTER TREATMENT WITH | | | |
|---|---|---|---|---|---|
| | | Control | Serotonin | IFN | Serotonin + IFN |
| 0 | 12 | 34 ± 1 | 34 ± 3 | 58 ± 3 | 60 ± 2 |
| 6 | 12 | 10 ± 2 | 31 ± 2 | 17 ± 1 | 52 ± 2 |
| 12 | 12 | 9 ± 1 | 31 ± 2 | 10 ± 1 | 52 ± 2 |

Table 2 shows the synergistic activation of NK cells by combined treatment with IFN-α and histamine. Monocytes were recovered along with NK cells in low-density Percoll fractions. In the experiment shown in Table 2, IFN-α and/or histamine was added to MNC obtained from these monocyte-containing Percoll fractions. As was the case with mixtures of eluted monocytes and low-density lymphocytes, IFN-α was relatively ineffective in these cell fractions, while histamine increased the cytotoxicity. Treatment of monocyte-containing cells with histamine ($10^{-4}$–$10^{-6}$ M) and IFN-α (25 U/ml) produced a synergistic NK-boosting response against K562 and against Daudi target cells. A similar result was obtained when histamine was replaced by serotonin.

In the results shown in Table 2, MNC from five different donors were used. All pounds were added to mixtures of MNC and target cells at the start of a 6 h (Daudi) or 16 h (K562) effecter and target cell incubation. The effecter cells were obtained from Percoll fractions 7–8, containing 33–55% monocytes.

FIG. 1 shows the synergistic NK cell activation by IFN-α and histamine/serotonin for different concentrations of IFN-α (0–100 U/ml). Cells from the monocyte-containing Percoll fraction 8 were incubated with culture medium, histamine ($10^{-4}$ M) or serotonin ($10^{-4}$ M) in the presence of The effect of histamine on monocyte-induced suppression of resting and IFN-α-activated NK cells was completely blocked by simultaneous treatment with the specific $H_2R$ antagonist ranitidine and imitated by the $H_2R$ agonist dimaprit, which is shown in Table 3. This means that the effect of histamine on the NK cell's response to IFN-α is $H_2R$-specific.

TABLE 3

Effects of Histamine and $H_2R$ Agonist Dimaprit and $H_2$-Antagonist Ranitidine on NK Cells

| | NKCC (Cell Lysis %) ± SEM AFTER TREATMENT WITH | | | |
|---|---|---|---|---|
| Treatment | Control | Ran | IFN | Ran + IFN |
| Control | 0.1 ± 0.1 | 0.0 ± 0.1 | 0.1 ± 0.1 | 0.0 ± 0.1 |
| Histamine | 9.4 ± 0.3 | 1.5 ± 0.3 | 31.7 ± 0.3 | 1.6 ± 0.2 |
| Dimaprit | 6.4 ± 1 | 0.4 ± 0.4 | 32.6 ± 1 | 0.5 ± 0.5 |

In the experiment shown in Table 3, culture medium (control), histamine ($10^{-4}$ M), dimaprit ($10^{-4}$ M), ranitidine (ran) ($10^{-4}$ M) and/or IFN-α (25 U/ml) were added at the start of a 6-hour $^{51}$Cr release assay using Daudi target cells. The data are representative of three similar experiments. NKCC is given as mean cell lysis %±SEM of six determinations. The effecter cells were recovered from a low-density Percoll fraction 8, containing around 40% monocytes.

Serotonin acted synergistically with IFN-α and had an effect corresponding to that of histamine. Ranitidine ($10^{-4}$ M) did not alter the effect of serotonin. The specific synthetic 5-$HT_{1A}$ R-agonists 8-OH-DPAT and (+)-ALK-3, which lack activity for 5-$HT_{1B}$R; 5-$HT_{1D}$R, 5-$HT_2$R or—$HT_3$R, intensified the baseline NKCC and restored the NK cell's response to IFN-α with a potency and effect comparable to that of serotonin. This is shown in Table 4. Ketanserin and ondansetron, which are antagonists of 5-$HT_2$R and 5-$HT_3$R, respectively, did not influence the effect of serotonin in equimolar concentrations.

TABLE 4

The Effect of Serotonin and 5-HT$_{1A}$R Agonists on NK Cells

| Treatment | NKCC AFTER TREATMENT WITH | |
|---|---|---|
|  | Medium | IFN |
| Medium | 1.1 ± 1 | 0.5 ± 0.3 |
| Serotonin 10$^{-4}$ M | 10.4 ± 1 | 44.3 ± 1 |
| Serotonin 10$^{-5}$ M | 4.5 ± 0.3 | 33.2 ± 1 |
| Serotonin 10$^{-6}$ M | 2.2 ± 0.4 | 12.3 ± 1 |
| 8-OH-DPAT 10$^{-4}$ M | 8.8 ± 1 | 43.3 ± 1 |
| (+)-ALK-3 10$^{-4}$ M | 9.1 ± 1 | 40.4 ± 1 |

In the experiment shown in Table 4, culture medium (control), scrotonin, 8-OH-DPAT (+)-ALK and/or IFN-α (25 U/ml) were added at the start of a 6-hour $^{51}$Cr-release assay against Daudi target cells. The NKCC is given as cell lysis %±SEM of six determinations. The effector cells were recovered from the low-density Percoll fraction 7, containing around 36% monocytes.

Similar experiments were then performed using freshly recovered human tumor cells as target cells, rather that the cultured tumor cell lines used as target cells in the experiments described above.

MNC were obtained from peripheral venous blood by Ficoll-Hypaque centrifuging and the mononuclear cells were separated into monocytes and NK-cell-enriched lymphocytes (Hellstrand et al., J. Interferon Res., 12, 199–206 1992). Seventy thousand NK-cell-enriched lymphocytes were mixed with 70,000 monocytes and 20,000 $^{51}$Cr-labeled leukemic target cells (97% pure acute myelogenous leukemic cells) in a total volume of 150 μl. The cells were treated with culture medium (control) or histamine dihydrochloride at a final concentration of 10$^{-4}$ M, during a 16 hour $^{51}$Cr-release assay to determine killed target cells.

Figure 2:
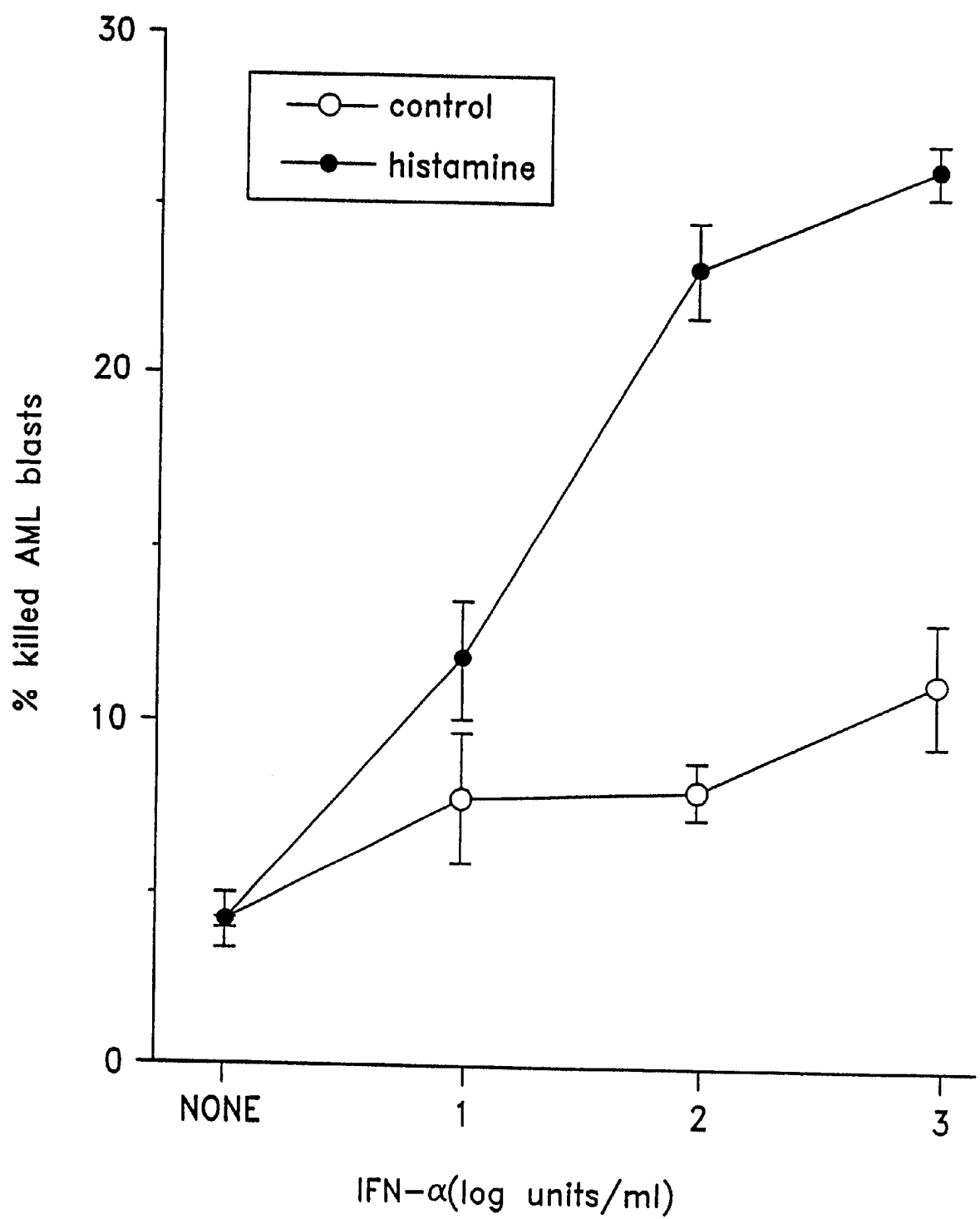
FIG. 2 shows in graph form the synergistic NK cell activation produced against freshly recovered human leukemic cells by IFN-α and histamine for various concentrations of IFN-α(0–100 U/ml).

The results are shown in FIG. 2. The data are the mean percent cell lysis of six determinations ±SEM. The recorded cytotoxicity was completely depleted after removal of NK-cells using DYNABEADS coated with anti-CD56, but not by removal of T-cells using beads coated with anti-CD3 (Hellstrand et al., Scand. J. Immunol., 37:7–18 (1993). As seen in FIG. 2, treatment with interferon alone does not induce killing of leukemic target cells unless histamine is present. In addition, it has been shown that the cytotoxic effects obtained with histamine and interferon-α are seen not only in cultured tumor cells, but in freshly recovered human leukemic cells as well.

Thus, in conclusion, it can be affirmed that the above-described in vitro experiments demonstrate that the biogenic amines histamine, through H$_2$ type receptors, and serotonin, through 5-HT$_{1A}$ type receptors, abolish the monocyte-induced suppression of resting and IFN-α activated NK cells. Treatment with IFN-α and compounds with H$_2$ or HT$_{1A}$ receptor agonist activity thus produces a synergistic activation of NK cells, which can be used in connection with tumor treatment or treatment of virus infections.

What is claimed is:

1. In a method of treating a viral infection in a patient through activation of NK cells, the improvement comprising administering to the patient an effective NK-cell-activity facilitating amount of a histamine H$_2$ or 5-HT$_{1A}$ receptor agonist.

2. The method of claim 1, wherein the receptor agonist is histamine.

3. The method of claim 1, wherein the receptor agonist is a histamine congener.

4. The method of claim 1, wherein the receptor agonist is serotonin.

5. The method of claim 1, wherein the receptor agonist is selected from the group consisting of dimaprit, clonidine, tolazoline, impromadine, 4-methylhistamine, betazole, 8-OH-DPAT (8-hydroxy-2-(di-n-propylamino)tetralin), ALK-3 (cis-8-hydroxy-1-methyl-2-(di-n-propylamino) tetralin), BMY 7378 (8[2-[4-(2-methoxyphenyl)-1-piperazinyl]ethyl]-8-azaspiro[4,5]decane-7,9-dione), NAN 190 (1-(2-methoxyphenyl-4-[4-(2-phthalimmido)butyl] pierazine HBr), lisuride, d-LSD, flesoxinan, DHE (dihydroergotamine), MDL 72832 (8-[4-91,4-benzodioxan-2-ylmethyl-amino)butyl]-8-azaspiro[4,5] decane-7,9-dione), 5-CT (5-carboxamidotryptamine), DP-5-CT (N,N-dipropyl-5-carboxamidotryptamine), ipsapirone, WB 4101 (2-[[[2-(2,6-dimethoxyphenoxy)ethyl]amino]methyl]-1,4-benzodioxane), ergotamine, buspirone, metergoline, spiroxatrine, PAPP (1-[2-(4-aminophenyl)ethyl]-4-(3-trifluoromethylphenyl) piperazine), SDZ (−) 21009 ((4(3-terbutylamino-2-hydroxypropoxy)indol-2-carbonic-acid-isopropylester), and butotenine.

6. The method of claim 1, wherein said receptor agonist is administered in a daily dose of between about 0.1 and 10 mg.

7. The method of claim 1, wherein said viral infection is a hepatitis virus infection.

8. The method of claim 7, wherein said hepatitis virus is hepatitis B.

9. The method of claim 7, wherein said hepatitis virus is hepatitis C.

10. A method for the treatment of hepatitis virus infections in vivo, comprising:

identifying a patient having a hepatitis virus infection, and
administering to said patient a first composition comprising interferon-α and a second composition having agonist activity for histamine H$_2$ or 5-HT$_{1A}$ receptors.

11. The method of claim 10, wherein said first composition is administered in a daily dose of about 1000 and 3000,000 U/kg.

12. The method of claim 10, wherein said second composition is administered in a daily dose of between about 0.1 and 10 mg.

13. The method of claim 10, wherein said first and second compositions are administered together.

14. The method of claim 10, wherein said first and second compositions are administered separately.

15. The method of claim 10, wherein said hepatitis virus is hepatitis B.

16. The method of claim 10, wherein said hepatitis virus is hepatitis C.

17. The method of claim 15, wherein the second composition comprises histamine.

18. The method of claim 16, wherein the second composition comprises histamine.

* * * * *